United States Patent [19]

Kemp et al.

[11] Patent Number: 5,102,849
[45] Date of Patent: Apr. 7, 1992

[54] SUPPORTED RARE EARTH AND PHOSPHORUS CATALYST

[75] Inventors: Richard A. Kemp, Stafford; Paul R. Weider, Houston, both of Tex.

[73] Assignee: Shell Oil Company, Houston, Tex.

[21] Appl. No.: 738,692

[22] Filed: Jul. 31, 1991

Related U.S. Application Data

[62] Division of Ser. No. 513,469, Apr. 23, 1990.

[51] Int. Cl.$^5$ .............................................. B01J 27/18
[52] U.S. Cl. ..................................... 502/214; 502/208
[58] Field of Search ................................ 502/208, 214

[56] References Cited

U.S. PATENT DOCUMENTS

| | | | |
|---|---|---|---|
| 3,752,878 | 8/1973 | Kehl et al. | 502/208 X |
| 3,933,932 | 1/1976 | Vrieland et al. | 502/208 X |
| 4,239,917 | 12/1980 | Yang | 568/618 |
| 4,302,613 | 11/1981 | Yang et al. | 568/618 |
| 4,306,093 | 12/1981 | Yang et al. | 568/618 |
| 4,375,564 | 3/1983 | Edwards | 568/618 |
| 4,453,022 | 6/1984 | McCain et al. | 568/618 |
| 4,453,023 | 6/1984 | McCain et al. | 568/618 |
| 4,456,697 | 6/1984 | Yang | 502/171 |
| 4,464,539 | 8/1984 | Hashimoto et al. | 502/208 X |
| 4,528,364 | 7/1985 | Prier | 528/370 |
| 4,658,065 | 4/1987 | Aoshima et al. | 564/487 |
| 4,721,817 | 1/1988 | Edwards | 518/618 |
| 4,886,917 | 12/1989 | Knopf et al. | 568/623 |
| 4,960,952 | 10/1990 | Kemp | 568/618 |
| 5,023,224 | 6/1991 | Kemp | 502/214 |
| 5,057,627 | 10/1991 | Edwards | 568/618 |

FOREIGN PATENT DOCUMENTS

0250168 12/1987 European Pat. Off. .

OTHER PUBLICATIONS

Zhang, et al., "Ring Opening Polymerization of Ethylene Oxide " by the $Y(P_{2O4})_3$—Al(i—Bu)$_3$—H$_2$O Catalyst, Inorganica Chemica Acta, 155, 1989, pp. 263-265.

*Primary Examiner*—W. J. Shine
*Assistant Examiner*—Douglas J. McGinty
*Attorney, Agent, or Firm*—Pamela J. McCollough

[57] ABSTRACT

Alkylene oxide adducts of organic compounds having active hydrogen atoms are prepared by a process which comprises contacting and reacting an alkylene oxide reactant comprising one or more vicinal alkylene oxides with an active hydrogen containing reactant comprising one or more compounds having active hydrogen atoms in the presence of a catalyst which comprises one or more compounds comprising a rare earth element and phosphorus supported on an inert porous support. The product alkoxylates are known to be useful, for instance, as nonionic surfactants, wetting and emulsifying agents, solvents, and chemical intermediates.

7 Claims, No Drawings

SUPPORTED RARE EARTH AND PHOSPHORUS CATALYST

This is a division, of application Ser. No. 513,469, filed Apr. 23, 1990.

FIELD OF THE INVENTION

This invention relates to an alkoxylation process in which alkylene oxides are reacted with compounds having active hydrogen atoms in the presence of catalysts comprising one or more compounds comprising a rare earth element and phosphorus supported on an inert porous support. In particularly preferred embodiments, the invention relates to processes for the preparation of alkoxylate products useful as nonionic surfactants.

BACKGROUND OF THE INVENTION

A large variety of products useful, for instance, as nonionic surfactants, wetting and emulsifying agents, solvents, and chemical intermediates, are prepared by the addition reaction (alkoxylation reaction) of alkylene oxides (epoxides) with organic compounds having one or more active hydrogen atoms. For example, particular mention may be made of the alkanol ethoxylates and alkyl-substituted phenol ethoxylates prepared by the reaction of ethylene oxide with aliphatic alcohols or substituted phenols of about 6 to 30 carbon atoms. Such ethoxylates, and to a lesser extent corresponding propoxylates and compounds containing mixed oxyethylene and oxypropylene groups, are widely employed as nonionic detergent components of commercial cleaning formulations for use in industry and in the home. As another example, the addition reaction of propylene oxide with polyols provides intermediates for the preparation of polyurethane products.

An illustration of the preparation of an alkanol ethoxylate (represented by formula III below) by addition of a number (n) of ethylene oxide molecules (formula II) to a single alkanol molecule (formula I) is presented by the equation

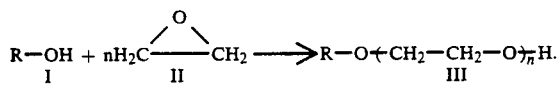

$$\text{R—OH} + n\text{H}_2\text{C}\overset{O}{\underset{}{\diagdown}}\text{CH}_2 \longrightarrow \text{R—O}(\text{CH}_2\text{—CH}_2\text{—O})_n\text{H}$$
I        II                        III The addition of alkylene oxides to alcohols and other active hydrogen containing compounds is known to be desirably promoted by a catalyst which is in conventional practice either basic or acidic in character. Recognized in the art as suitable basic catalysts are the basic compounds of the alkali metals of Group I of the Periodic Table, e.g., sodium, potassium, rubidium, and cesium, and the basic salts of certain of the alkaline earth metals of Group II of the Periodic Table, e.g., calcium, strontium, barium and in some cases magnesium. Conventional acidic alkoxylation catalysts include, broadly, Lewis acid or Friedel-Crafts catalysts. Specific examples of these acid catalysts are the fluorides, chlorides, and bromides of boron, antimony, tungsten, iron, nickel, zinc, tin, aluminum, titanium and molybdenum. The use of complexes of such halides with, for example, alcohols, ethers, carboxylic acids, and amines has also been reported. Still other examples of known acidic alkoxylation catalysts are sulfuric and phosphoric acids; perchloric acid and the perchlorates of magnesium, calcium, manganese, nickel and zinc; certain metal oxalates, sulfates, phosphates, carboxylates and acetates; alkali metal fluoroborates; zinc titanate; and certain metal salts of benzene sulfonic acid.

Other art on the subject of alkoxylation includes U.S. Pat. No. 4,727,199, which describes a process for reacting a liquid or solid alkylene oxide with a liquid or gaseous active hydrogen compound in the presence of a catalytic amount of an anion-bound metal oxide heterogenous catalyst, wherein the anion is $SO_4$, $BF_4$, $CO_3$, $BO_3$, $PO_4$, $SeO_4$, $MoO_4$, $B_4O_7$ or $PF_6$ and the metal oxide is an oxide of zirconium, nickel, aluminum, tin, calcium, magnesium, iron, titanium, thorium, hafnium, or rubidium. Still other prior art describes the use of zeolitic materials as alkoxylation catalysts, while European patent application 0250168 and other art cited therein disclose lamellar clay catalysts.

Alkylene oxide addition reactions are known to produce a product mixture of various alkoxylate molecules having different numbers of alkylene oxide adducts (oxyalkylene adducts), e.g., having different values for the adduct number n in formula III above. The adduct number is a factor which in many respects controls the properties of the alkoxylate molecule, and efforts are made to tailor the average adduct number of a product and/or the distribution of adduct numbers within a product to the product's intended service. In certain preferred embodiments, the present invention provides a process characterized by enhanced selectivity for the preparation of alkoxylate mixtures in which a relatively large proportion of the alkoxylate molecules has a number (n) of alkylene oxide adducts that is within a relatively narrow range of values.

It is known in the art that alcohol alkoxylate products having a narrow range alkylene oxide adduct distribution are preferred for use in certain detergent formulations (Great Britain Patent No. 1,462,134; Derwent Publications Research Disclosure number 194,010). Narrow-range alcohol alkoxylates are also known to be particularly valuable as chemical intermediates in the synthesis of certain carboxyalkylated alkyl polyethers (U.S. Pat. No. 4,098,818) and of certain alkyl ether sulfates (Great Britain Patent No. 1,553,561). Conventional commercial alkoxylate preparation, which has in large part been limited to the use of basic catalysts, particularly the metals sodium and potassium and their oxides and hydroxides, yields only a relatively broad distribution range product. Conventional acid-catalyzed alkoxylation reactions have long been known to produce a more narrow range product than that obtained with the alkali metal catalysts. However, acid catalysts have substantial disadvantages in several other respects. For instance, the acids are often unstable with limited life and effectiveness as catalysts in the alkoxylation mixture. Both the acid catalysts themselves and their decomposition products catalyze side reactions producing relatively large amounts of polyalkylene glycols, and also react directly with the components of the alkoxylation mixture to yield undesirable, and often unacceptable, by-products such as organic derivatives of the acids and dioxane.

Also of substantial importance in alkoxylation processes is the ability of the process to minimize the quantity of unreacted (or residual) active hydrogen reactant remaining in the final product. A high level of residual reactant either represents a loss of valuable reactant, or requires that further processing of the product be carried out to recover the reactant. Moreover, the presence of the unreacted material is often a disadvantage from the standpoint of product quality and environmental concerns. For instance, residual alkanol in a detergent alcohol ethoxylate product contributes to volatile organic emissions during spray drying of detergent formulations.

It has recently been reported in the art that, in addition to conventional acidic catalysts, a number of other substances have been found to function as catalysts or in co-catalyst combinations which are capable of producing relatively narrow distributions for the oxyalkylene adducts of higher alkanols and other active hydrogen containing compounds. For instance, it has recently been disclosed (U.S. Pat. Nos. 4,306,093 and and 4,239,917, and published European Patent Application Nos. 0026544, 0026546, 0026547) that certain compounds of barium, strontium, and calcium promote narrow-range alkoxylation products. U.S. Pat. Nos. 4,210,764 and 4,223,164 describe the use of cresylic acids to promote alkoxylation catalyzed by barium and strontium compounds. U.S. Pat. No. 4,302,613 discloses that a more peaked reaction product can be obtained by combining barium and strontium alkoxylation catalysts with co-catalysts such as calcium oxide, calcium carbide, calcium hydroxide, magnesium metal, magnesium hydroxide, zinc oxide and aluminum metal. U.S. Pat. No. 4,453,023 describes a process for preparing alkoxylates having a narrower molecular weight distribution which employs a catalyst comprising a barium compound and a promoter selected from the class consisting of superphosphoric acid, phosphoric acid, diphosphoric acid, triphosphoric acid, phosphorous acid, dihydrogen phosphate compounds, oxides of phosphorus, carbon dioxide, and oxalic acid. U.S. Pat. No. 4,453,022 describes a similar process wherein the catalyst comprises a calcium or strontium compound and a promoter selected from the class consisting of superphosphoric acid, phosphoric acid, diphosphoric acid, triphosphoric acid, phosphorous acid, dihydrogen phosphate compounds, oxides of phosphorus, sulfuric acid, bisulfate compounds, carbonic acid, bicarbonate compounds, carbon dioxide, oxalic acid and oxalic acid salts, sulfur trioxide, sulfur dioxide, and sulfurous acid. Published PCT application WO 85/00365 discloses other activated calcium containing alkoxylation catalysts capable of producing narrow range alkoxylation products. U.S. Pat. No. 4,375,564 reports that a narrow range product results from alkoxylation reactions catalyzed by a magnesium compound in combination with a compound of one of the elements aluminum, boron, zinc, titanium, silicon, molybdenum, vanadium, gallium, germanium, yttrium, zirconium, niobium, cadmium, indium, tin, antimony, tungsten, hafnium, tantalum, thallium, lead and bismuth. U.S. Pat. No. 4,483,941 discloses catalysts for alkoxylation reactions which comprise either $BF_3$ or $SiF_4$ in combination with an alkyl or alkoxide compound of aluminum, gallium, indium, thallium, titanium, zirconium, and hafnium. U.S. Pat. No. 4,456,697 describes an alkoxylation catalyst which comprises a mixture of HF and one or more metal alkoxides. Japanese patent specification 52051307 to Tokuyama Soda KK discloses the selective preparation of mono- rather than di- or tri-alkylene glycol esters from alkylene oxide and alcohol using solid acid catalysts such as silica, alumina, titania, vanadium pentoxide, antimony pentoxide, titanyl sulfate, tungstic acid, phosphotungstic acid, and silver perchlorite.

U.S. Pat. No. 4,721,816 claims a process for preparing narrow range distribution alkoxylates, wherein the catalyst is a combination of one or more sulfur-containing acids with one or more aluminum alcoholate or phenolate compounds. U.S. Pat. No. 4,721,817 claims a similar process wherein the combination contains one or more phosphorus-containing acids.

U.S. Pat. Nos. 4,665,236 and 4,689,435 describes a process for the alkoxylation of active hydrogen reactants using certain bimetallic oxo catalysts. The catalysts described in U.S. Pat. No. 4,665,236 include compounds in which one of the metal species in the bimetallic molecule is lanthanum, and European application 0250168 discloses lamellar clay catalysts which have been ion exchanged with lanthanum and other rare earth elements.

The alkoxylation catalysts discussed above are catalysts which are either dissolved or dispersed as fine particulate material throughout the alkoxylation reaction mixture. The removal of these catalysts from the reaction product has proven to be quite difficult. In addition, these catalysts cannot be recycled.

The present invention relates to a catalyst in which the catalytically active material is attached to an inert porous support. The present invention particularly relates to an alkoxylation reaction catalyzed by one or more compounds comprising a rare earth element and phosphorus supported on an inert porous support. The catalyst of the present invention is advantageous in that the alkoxylation reaction product can be easily removed from the catalyst bed and the catalyst can be recycled.

SUMMARY OF THE INVENTION

It has been found that one or more compounds comprising a rare earth element and phosphorus supported on an inert support are effective catalysts for the addition reaction of alkylene oxides with organic compounds having active hydrogen atoms. It has further been found that, in certain preferred embodiments, an alkoxylation reaction catalyzed by one or more compounds comprising a rare earth element and phosphorus supported on an inert porous support provides an alkoxylate product, particularly an alkanol ethoxylate product, of exceptionally narrow-range alkylene oxide adduct distribution.

The present invention is particularly directed to a process for the preparation of alkoxylates of active hydrogen containing organic compounds which comprises contacting an alkylene oxide reactant comprising one or more vicinal alkylene oxides with an active hydrogen reactant comprising one or more organic compounds (e.g., alcohols, phenols, thiols, amines, polyols, carboxylic acids, etc.) having one or more active hydrogen atoms, in the presence of a catalyst which comprises one or more compounds comprising a rare earth element and phosphorus deposited on an inert porous support.

As the terminology is used herein, the "rare earth" elements are those of atomic numbers 57 through 71. As used herein, the terms "rare earth" and "lanthanide" are used interchangeably.

DESCRIPTION OF THE PREFERRED EMBODIMENTS

The present invention centers upon discoveries associated with the use in an alkoxylation process of a certain class of catalysts. Apart from the use of such catalysts, the process of the invention is, as a general rule, suitably conducted using such reactants and practicing under such processing procedures and reaction conditions as are well known to the art for alkoxylation reactions. Certain preferences may, however, be expressed for particular reactants, procedures and conditions.

Thus, for instance, the invention is preferably applied to processes utilizing an alkylene oxide (epoxide) reactant which comprises one or more vicinal alkylene oxides, particularly the lower alkylene oxides and more particularly those in the $C_2$ to $C_4$ range. In general, the alkylene oxides are represented by the formula

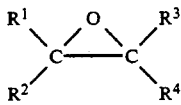

wherein each of the $R^1$, $R^2$, $R^3$ and $R^4$ moieties is individually selected from the group consisting of hydrogen and alkyl moieties. Reactants which comprise ethylene oxide, propylene oxide, or mixtures of ethylene oxide and propylene oxide are more preferred, particularly those which consist essentially of ethylene oxide and propylene oxide. Alkylene oxide reactants consisting essentially of ethylene oxide are considered most preferred from the standpoint of commercial opportunities for the practice of alkoxylation processes, and also from the standpoint of the preparation of products having narrow-range ethylene oxide adduct distributions.

Likewise, the active hydrogen reactants suitably utilized in the process of the invention include those known in the art for reaction with alkylene oxides and conversion to alkoxylate products. Suitable classes of active hydrogen reactants include (but are not necessarily limited to) alcohols, phenols, thiols (mercaptans), amines, polyols, carboxylic acids, and mixtures thereof. Preference generally exists for use of hydroxyl-containing reactants. More preferably, the active hydrogen containing reactant consists essentially of one or more active hydrogen containing compounds selected from the group consisting of alkanols, alkyl polyols and phenols (including alkyl-substituted phenols).

Among the suitable carboxylic acids, particular mention may be made of the mono- and dicarboxylic acids, both aliphatic (saturated and unsaturated) and aromatic. Specific examples include acetic acid, propionic acid, butyric acid, valeric acid, caproic acid, lauric acid, myristic acid, palmitic acid, stearic acid, oleic acid, rosin acids, tall oil acids, terephthalic acid, benzoic acid, phenylacetic acid, toluic acid, acrylic acid, methacrylic acid, crotonic acid, maleic acid, and the like.

Among the suitable amines, particular mention may be made of primary, secondary and tertiary alkylamines and of alkylamines containing both amino and hydroxyl groups, e.g., N,N-di(n-butyl)-ethanolamine and tripropanolamine.

Among the suitable thiols, particular mention may be made of primary, secondary and tertiary alkane thiols having from 1 to about 30 carbon atoms, particularly those having from about 8 to 20 carbon atoms. Specific examples of suitable tertiary thiols are those having a highly branched carbon chain which are derived via hydrosulfurization of the products of the oligomerization of lower olefins, particularly the dimers, trimers, and tetramers and pentamers of propylene and the butylenes. Secondary thiols are exemplified by the lower alkane thiols, such as 2-propanethiol, 2-butanethiol, and 3-pentanethiols, as well as by the products of the hydrosulfurization of the substantially linear oligomers of ethylene as are produced by the Oxo process. Representative but not limiting examples of thiols derived from ethylene oligomers include the linear carbon chain products, such as 2-decanethiol, 3-decanethiol, 4-decanethiol, 5-decanethiol, 3-dodecanethiol, 5-dodecanethiol, 2-hexadecanethiol, 5-hexadecanethiol and 8-octadencanethiol, and the branched carbon chain products, such as 2-methyl-4-tridecanethiol. Primary thiols are typically prepared from terminal olefins by hydrosulfurization under free-radical conditions and include, for example, 1-butanethiol, 1-hexanethiol, 1-dodecanethiol, 1-tetradecanethiol and 2-methyl-1-tridecanethiol.

Among the polyols, particular mention may be made of those having from 2 to about 6 hydroxyl groups. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like.

The alcohols (both mono- and poly-hydroxy) and the phenols (including alkyl-substituted phenols) are preferred classes of active hydrogen reactants for purposes of the invention. Among the phenols, particular mention may be made of phenol and of alkyl-substituted phenols wherein each alkyl substituent has from one to about 30 (preferably from one to about 20) carbon atoms, for example, p-methylphenol, p-ethylphenol, p-hexylphenol, nonylphenol, p-decylphenol, didecyl phenol and the like.

Acyclic aliphatic mono-hydric alcohols (alkanols) form a most preferred class of reactants, particularly the primary alkanols, although secondary and tertiary alkanols are also very suitably utilized in the process of the invention. Preference can also be expressed, for reason of both process performance and commercial value of the product, for alkanols having from one to about 30 carbon atoms, with $C_6$ to $C_{24}$ alkanols considered more preferred and $C_8$ to $C_{20}$ alkanols considered most preferred. As a general rule, the alkanols may be of branched or straight chain structure, although preference further exists for alkanol reactants in which greater than about 50 percent, more preferably greater than about 60 percent, and most preferably greater than about 70 percent of the molecules are of linear (straight-chain) carbon structure.

The general suitability of such alkanols as reactants in alkoxylation reactions is well recognized in the art. Commercially available mixtures of primary monohydric alkanols prepared via the oligomerization of ethylene and the hydroformylation or oxidation and hydrolysis of the resulting higher olefins are particularly preferred. Examples of commercially available alkanol mixtures include the NEODOL Alcohols, trademark of and sold by Shell Chemical Company, including mixtures of $C_9$, $C_{10}$ and $C_{11}$ alkanols (NEODOL 91 Alcohol), mixtures of $C_{12}$ and $C_{13}$ alkanols (NEODOL 23 Alcohol), mixtures of $C_{12}$, $C_{13}$, $C_{14}$, and $C_{15}$ alkanols (NEODOL 25 Alcohol), and mixtures of $C_{14}$ and $C_{15}$ alkanols (NEODOL 45 Alcohol); the ALFOL Alcohols, trademark of and sold by Vista Chemical Company, including mixtures of $C_{10}$ and $C_{12}$ alkanols (ALFOL 1012), mixtures of $C_{12}$ and $C_{14}$ alkanols (ALFOL 1214), mixtures of $C_{16}$ and $C_{18}$ alkanols (ALFOL 1618), and mixtures of $C_{16}$, $C_{18}$ and $C_{20}$ alkanols (ALFOL 1620); the EPAL Alcohols, trademark of and sold by Ethyl Chemical Company, including mixtures of $C_{10}$ and $C_{12}$ alkanols (EPAL 1012), mixtures of $C_{12}$ and $C_{14}$ alkanols (EPAL 1214), and mixtures of $C_{14}$, $C_{16}$, and $C_{18}$ alkanols (EPAL 1418); and the TERGITOL-L Alcohols, trademark of and sold by Union Carbide Corporation, including mixtures of $C_{12}$, $C_{13}$, $C_{14}$, and $C_{15}$ alkanols (TERGITOL-L 125). Also very suitable are the commercially available alkanols prepared by the reduction of naturally occurring fatty esters, for example, the CO and TA products of Procter and Gamble Company and the TA alcohols of Ashland Oil Company.

Among the polyols, particular mention may be made of those having from 2 to about 6 hydroxyl groups and 2 or more, preferably 2 to 30 carbon atoms. Specific examples include the alkylene glycols such as ethylene glycol, propylene glycol, hexylene glycol, and decylene glycol, the polyalkylene glycol ethers, such as diethylene glycol, triethylene glycol, propylene glycol, dipropylene glycol, tripropylene glycol, glycerine, sorbitol, and the like. Higher oligomers and polymers of the polyols are also very suitable.

The active hydrogen containing reactant is also very suitably the alkoxylate product of a previous alkoxylation of an active hydrogen containing compound.

Further examples of both specific alkylene oxide reactants and specific active hydrogen containing reactants suitable for use in this invention are recited in the aforementioned U.S. patents, the relevant disclosures of which are incorporated herein by this reference.

The alkylene oxide reactant and the active hydrogen reactant are contacted in the presence of a catalyst comprising one or more compounds comprising a rare earth element and phosphorus supported on an inert porous support. As used herein, "supported on an inert porous support" means that the rare earth element and/or phosphorus are on the external surface and/or the internal pore surface of the support. It is understood that all of the rare earth element and/or phosphorus may be on the external surface of the support, or a portion of the rare earth element and/or phosphorus may be on the external surface of the support and a portion may be incorporated into the internal pore surface of the support. It is further understood that a portion, but not all, of the rare earth element and/or phosphorus may be incorporated into the matrix of the support.

The catalysts in the instant invention can be suitably prepared using any conventional technique such as, for example, impregnation whereby the rare earth element and phosphorus are deposited on the support; coprecipitation, comulling, spray drying, and the like whereby the rare earth element and phosphorus are incorporated into the support as well as on the surface of the support; or any combination of these conventional techniques.

In a preferred embodiment, at least one of the compound(s) comprising a rare earth element and phosphorus which are attached to the inert porous support is a rare earth phosphate. In a more preferred embodiment, the rare earth phosphate is selected from the group consisting of lanthanum phosphate, cerium phosphate, neodymium phosphate, samarium phosphate, gadolinium phosphate, dysprosium phosphate and mixtures thereof. In a particularly preferred embodiment, the rare earth phosphate is lanthanum phosphate.

The catalysts of the instant invention are typically prepared by impregnating an inert porous support with one or more rare earth compounds dissolved in a suitable solvent sufficient to cause deposition on the support of from about 0.5 percent by weight to about 36 percent by weight, preferably from about 6 percent by weight to about 24 percent by weight, basis total catalyst, of rare earth element. Also deposited on the support subsequent to the deposition of rare earth element is one or more phosphorus compounds dissolved in a suitable solvent sufficient to cause deposition on the support of from about 0.1 percent by weight to about 8 percent by weight, preferably from about 1 percent by weight to about 6 percent by weight, basis total catalyst, of phosphorus. The remainder of the catalyst comprises residual oxygen and support materials.

The support employed for these catalysts in its broadest aspects is selected from the large number of porous refractory catalysts carriers or support materials which are considered relatively inert in the presence of alkoxylation process feeds, products and reaction conditions. Suitable examples of inert porous supports include alumina, silica, silica-alumina, titania, zirconia, magnesia and the like, and mixtures thereof.

In a preferred embodiment, the supported rare earth and phosphorus-containing catalyst is prepared by impregnating an inert porous support with a solution of a lanthanide compound, preferably lanthanide nitrate, lanthanide carbonate, lanthanide chloride or lanthanide hydroxide, calcining the impregnated material at a temperature in the range of from about 100° C. to about 700° C. to yield a supported lanthanide oxide, impregnating the supported lanthanide oxide with a solution of a phosphorus compound, preferably phosphoric acid, and then drying at a temperature in the range of from about 50° C. to about 200° C. to yield the supported lanthanide and phosphorus-containing catalyst.

In a particularly important embodiment, the invention is a process which comprises contacting and reacting an alkylene oxide reactant (particularly a reactant comprising ethylene oxide, propylene oxide, or a mixture of propylene oxide and ethylene oxide) with an active hydrogen containing reactant (particularly an alcohol, polyol, or other hydroxyl containing compound), in the presence of a catalyst which comprises one or more compounds comprising lanthanum and phosphorus supported on an inert porous support, wherein said catalyst contains from about 0.5 percent by weight to about 36 percent by weight, preferably about 6 percent by weight to about 24 percent by weight, basis total catalyst, of lanthanum, and from about 0.1 percent by weight to about 8 percent by weight, preferably about 1 percent by weight to about 6 percent by weight, basis total catalyst, of phosphorus. In a most preferred embodiment, ethylene oxide is contacted with a $C_1$ to $C_{30}$ primary alkanol in the presence of a supported lanthanum phosphate catalyst.

In terms of processing procedures, the alkoxylation reaction in the invention may be conducted in a generally conventional manner. The process can be carried out either batchwise or continuously, using a fixed catalyst bed, or a stirrer equipped reactor or other mobile catalyst contacting process as well as any other well known contacting technique. For example, the liquid active hydrogen reactant may initially be contacted with the catalyst. The catalyst and liquid reactant are contacted, preferably under agitation, with alkylene oxide reactant, which is typically introduced in gaseous form, at least for the lower alkylene oxides. The order in which the reactants and catalyst are contacted has not been found to be critical to the invention.

Overall, the two reactants are utilized in quantities which are predetermined to yield an alkoxylate product of the desired mean or average adduct number. The average adduct number of the product is not critical to this process. Such products commonly have an average adduct number in the range from less than one to about 30 or greater.

In general terms, suitable and preferred process temperatures and pressures for purposes of this invention are the same as in conventional alkoxylation reactions between the same reactants, employing conventional catalysts. A temperature of at least about 90° C., particularly at least about 120° C. and most particularly at least about 130° C., is typically preferred from the standpoint of the rate of reaction, while a temperature less than about 250° C., particularly less than about 210° C., and most particularly less than about 190° C., is typically desirable to minimize degradation of the product. As is known in the art, the process temperature can be optimized for given reactants, taking such factors into account.

Super-atmospheric pressures, e.g., pressures between about 10 and 150 psig, are preferred, with pressure being sufficient to maintain the active hydrogen reactant substantially in the liquid state.

When the active hydrogen reactant is a liquid and the alkylene oxide reactant is a vapor, alkoxylation is then suitably conducted by introducing alkylene oxide into a pressure reactor containing the liquid active hydrogen reactant and the catalyst. For considerations of process safety, the partial pressure of a lower alkylene oxide reactant is preferably limited, for instance, to less than about 60 psia, and/or the reactant is preferably diluted with an inert gas such as nitrogen, for instance, to a vapor phase concentration of about 50 percent or less. The reaction can, however, be safely accomplished at greater alkylene oxide concentration, greater total pressure and greater partial pressure of alkylene oxide if suitable precautions, known to the art, are taken to manage the risks of explosion. A total pressure of between about 40 and 110 psig, with an alkylene oxide partial pressure between about 15 and 60 psig, is particularly preferred, while a total pressure of between about 50 and 90 psig, with an alkylene oxide partial pressure between about 20 and 50 psig, is considered more preferred.

The time required to complete a process according to the invention is dependent both upon the degree of alkoxylation that is desired (i.e., upon the average alkylene oxide adduct number of the product) as well as upon the rate of the alkoxylation reaction (which is, in turn dependent upon temperature and nature of the reactants). A typical reaction time for preferred embodiments is in the range from 1 to 24 hours. After the ethoxylation reaction has been completed, the product is preferably cooled and the catalyst is removed. The catalyst can then be filtered and recycled.

The following Examples are provided to further illustrate certain specific aspects of the invention but are not intended to limit its broader scope.

EXAMPLE 1

A catalyst having compounds of the lanthanide metals and phosphorus supported on silica spheres was prepared by the following procedure. To 20.2 grams of hydroxylated silica spheres, which has been dried at 122° C. under vacuum, were added 64.8 grams of an aqueous solution of lanthanide nitrates (1.71 mmol of lanthanides/gram solution; 95% lanthanum, 5% a mixture of other lanthanides). This was tumbled to allow the solution to penetrate the silica spheres and then dried in the air at 120° C. The impregnated silica spheres were calcined in air at 600° C. for 15 hours. This afforded 36.8 grams of pale blue pellets. These pellets were wetted with 100 ml of de-ionized water followed by the addition of 200 ml of 0.75M phosphoric acid. The stagnant solution was allowed to react for 2.5 hours. The resulting supported catalyst was isolated by filtration and washed with de-ionized water until the rinses were neutral. The pellets were dried in vacuo at 50° C. and 5 mm Hg to afford 44.24 grams of blue pellets. X-ray diffraction data indicated the presence of lanthanum phosphate as did surface infrared spectroscopy.

An alkoxylation process in accordance with the invention was conducted under the following procedures. The alkalene oxide reactant for this process embodiment consisted of ethylene oxide and the active hydrogen containing reactant consisted of NEODOL 23 Alcohol (NEODOL is a trademark of Shell Chemical Company) characterized as a mixture of primary, 80% linear (20% branched), alkanols having twelve and thirteen carbon atoms (about 40% by mol $C_{12}$ and 60% by mol $C_{13}$).

Initially, 2.85 grams of the pellets prepared as described above were added to 110 grams of NEODOL 23 Alcohol, and the mixture was heated in a 500 milliliter autoclave to 155° C. under a nitrogen sparge to drive off the water. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied upon demand to maintain a constant mole percent composition of ethylene oxide in the gas cap. Temperature was maintained at 155° C. A total of 175 grams of ethylene oxide was taken up over a period of 70 minutes. The reactor was maintained for an additional 45 minutes to consume un-reacted ethylene oxide in the system.

The product was analyzed by GC-LC techniques and found to have a mean average adduct number of 6.5. The ethylene oxide adduct distribution of the product is presented in the following table.

| ETHOXYLATE DISTRIBUTION | |
| --- | --- |
| Adduct Number | Concentration |
| 0 (Residual Alcohol) | 2.6% wt |
| 1 | 0.6 |
| 2 | 0.7 |
| 3 | 1.5 |
| 4 | 4.0 |
| 5 | 9.6 |
| 6 | 16.8 |
| 7 | 20.5 |
| 8 | 17.3 |
| 9 | 11.5 |
| 10 | 6.6 |
| 11 | 3.6 |
| 12 | 1.9 |
| 13 | 1.2 |
| 14 | 0.7 |
| 15 | 0.5 |
| 16 | 0.4 |

EXAMPLE 2

An experimental series demonstrating the ease with which the catalyst in Example 1 may be recycled was performed by adding 5.0 grams of the pellets prepared as described above to 110 grams of NEODOL 23 Alcohol. The mixture was heated in a 500 milliliter autoclave to 155° C. under a nitrogen sparge to drive off the water. A mixture of nitrogen and ethylene oxide was then introduced into the reactor to a total pressure of 75 psia (45 psia nitrogen and 30 psia ethylene oxide). Alkoxylation (ethoxylation) commenced immediately. Additional ethylene oxide was supplied upon demand to maintain a constant mole percent composition of ethylene oxide in the gas cap. Temperature was maintained at 155° C. The reaction was run until a total of 175 grams of ethylene oxide was taken up. The reactor was maintained for an additional 45 minutes to consume unreacted ethylene oxide in the system. The catalyst was recycled by simply decanting the supernatant liquid (the warm product ethoxylate) from the catalyst particles, adding 110 grams of fresh NEODOL 23 Alcohol to the catalyst particles, and performing a subsequent ethoxylation as described. The stirrer employed in the 500 milliliter autoclave caused mechanical degradation of the catalyst spheres during the multiple recycle.

These products were analyzed by GC-LC techniques. The ethylene oxide adduct distribution of these products is presented in the following table.

| ETHOXYLATE DISTRIBUTION | | | | |
|---|---|---|---|---|
| | Concentration (% wt) | | | |
| Adduct Number | Initial Run | First Recycle | Second Recycle | Third Recycle |
| 0 | 3.1 | 3.3 | 3.0 | 3.3 |
| 1 | 0.9 | 0.8 | 1.2 | 1.2 |
| 2 | 1.0 | 1.1 | 1.1 | 1.1 |
| 3 | 2.3 | 2.6 | 2.6 | 2.6 |
| 4 | 6.0 | 6.9 | 6.8 | 6.7 |
| 5 | 13.0 | 13.5 | 13.1 | 12.7 |
| 6 | 20.5 | 18.9 | 18.9 | 17.3 |
| 7 | 21.6 | 18.4 | 18.9 | 17.3 |
| 8 | 16.0 | 13.8 | 14.3 | 13.8 |
| 9 | 8.7 | 8.7 | 9.1 | 9.6 |
| 10 | 3.95 | 5.3 | 5.2 | 6.1 |
| 11 | 1.7 | 2.9 | 2.8 | 3.5 |
| 12 | 0.7 | 1.6 | 1.5 | 2.1 |
| 13 | 0.3 | 0.9 | 0.8 | 1.3 |
| 14 | 0.21 | 0.6 | 0.5 | 0.8 |
| 15 | 0.1 | 0.4 | 0.3 | 0.5 |
| 16 | | 0.3 | 0.1 | 0.3 |
| Average Adduct Number | 5.9 | 6.0 | 6.0 | 6.0 |
| Time of Reaction (Minutes) | 57 | 60 | 75 | 98 |

EXAMPLE 3

A catalyst having compounds of the lanthanide elements and phosphorus supported on α-alumina rings was prepared according to the following procedure. To 25 grams of α-alumina rings (UCI Catalyst Support SAHM-467) were added 18.9 grams of an aqueous solution of lanthanide nitrates (1.71 mmol of lanthanides/gram of solution; 95% lanthanum, 5% a mixture of other lanthanides). This was tumbled to allow the solution to penetrate the α-alumina rings and then dried in the air at 120° C. The impregnated alumina rings were calcined in air at 700° C. for 5 hours. This afforded 30.2 grams of pale blue rings. These rings were wetted with 150 ml of deionized water followed by the addition of 25 ml of 2M phosphoric acid. The supernatant of the reaction mixture was gently stirred while the supported oxide was allowed to react for 15 minutes. The resulting supported catalyst was isolated by filtration and washed with de-ionized water until the rinses were neutral. The rings were dried in vacuo at 50° C. and 5 mm Hg to afford 31.32 grams of blue rings. X-ray diffraction data did not indicate the presence of lanthanum phosphate, but surface infrared spectroscopy showed patterns characteristic of lanthanum phosphate.

Ten grams of these pellets were added to 110 grams of NEODOL 23 Alcohol. An ethoxylation reaction was then carried out according to the procedures described in Example 1. A total of 175 grams of ethylene oxide was consumed over a period of 2 hours at 170° C. The product had a mean average adduct number of 6.2. The adduct distribution of this product is presented in the following table.

| ETHOXYLATE DISTRIBUTION | |
|---|---|
| Adduct Number | Concentration |
| 0 (Residual Alcohol) | 3.3% wt |
| 1 | 0.7 |
| 2 | 0.9 |
| 3 | 2.4 |
| 4 | 6.6 |
| 5 | 13.3 |
| 6 | 18.1 |
| 7 | 17.1 |
| 8 | 12.7 |
| 9 | 8.2 |
| 10 | 5.0 |
| 11 | 3.1 |
| 12 | 2.0 |
| 13 | 1.4 |
| 14 | 1.0 |
| 15 | 0.8 |
| 16 | 0.5 |

EXAMPLE 4

A catalyst having compounds of the lanthanide metals and phosphorus supported on diatomaceous earth was prepared by the following procedure. To 31.3 grams of Celite (Celite is the trademark of the Manville Corporation), which had been dried at 600° C. in nitrogen for 5 hours, were added 70.1 grams of an aqueous solution of lanthanide nitrates (1.71 mmol of lanthanides/gram of solution; 95% lanthanum, 5% a mixture of other lanthanides). This was mixed to allow the solution to penetrate the Celite. The impregnated powder was calcined in air at 600° C. for 5 hours. This afforded 49.1 grams of a white solid. The solid was wetted with 200 ml of deionized water followed by the addition of 50 ml of 2.8M phosphoric acid. The slurry was allowed to react for 30 minutes. The resulting supported catalyst was isolated by filtration and washed with de-ionized water until the rinses were neutral. The powder obtained was dried in vacuo at 50° C. and 5 mm Hg to afford 55.6 grams of a blue powder.

To 110 grams of NEODOL 23 Alcohol were added 3.6 grams of the Celite supported catalyst prepared as described above. An ethoxylation reaction was then carried out according to the procedures described in Example 1. A total of 175 grams of ethylene oxide was consumed over a period of 50 minutes at 155° C. The product had a means average adduct number of 6.6. The adduct distribution of this product is presented in the following table.

| ETHOXYLATE DISTRIBUTION | |
| --- | --- |
| Adduct Number | Concentration |
| 0 (Residual Alcohol) | 2.5% wt |
| 1 | 0.6 |
| 2 | 0.6 |
| 3 | 1.1 |
| 4 | 2.9 |
| 5 | 8.0 |
| 6 | 16.9 |
| 7 | 23.2 |
| 8 | 20.5 |
| 9 | 12.8 |
| 10 | 6.2 |
| 11 | 2.6 |
| 12 | 1.1 |
| 13 | 0.5 |
| 14 | 0.3 |
| 15 | 0.2 |
| 16 | 0.1 |

EXAMPLE 5

A catalyst having compounds of the lanthanide metals and phosphorus supported on the rutile form of titanium (IV) oxide was prepared by the following procedure. To 21.6 grams of titanium oxide were added 18.6 grams of an aqueous solution of lanthanide nitrates (1.71 mmol of lanthanides/gram of solution; 95% lanthanum, 5% a mixture of other lanthanides). the impregnated powder was calcined at 600° C. in flowing air for 5 hours. This afford 26.4 grams of a blue solid. The solid was wetted with 100 ml of deionized water followed by the addition of 50 ml of 0.75M phosphoric acid. The slurry was allowed to react for 30 minutes. The resulting supported catalyst was isolated by filtration and washed with de-ionized water until the rinses were neutral. The powder obtained was dried in vacuo at 50° C. and 5 mm Hg to afford 27.0 grams of a white powder.

To 110 grams of NEODOL 23 Alcohol were added 7.8 grams of the supported catalyst prepared as described above. An ethoxylation reaction was then carried out according to the procedures described in Example 1. A total of 175 grams of ethylene oxide was consumed over a period of 70 minutes at 155° C. The product had a mean average adduct number of 6.0. The adduct distribution of this product is presented in the following table.

| ETHOXYLATE DISTRIBUTION | |
| --- | --- |
| Adduct Number | Concentration |
| 0 (Residual Alcohol) | 3.5% wt |
| 1 | 0.8 |
| 2 | 0.9 |
| 3 | 2.3 |
| 4 | 6.6 |
| 5 | 13.7 |
| 6 | 19.5 |
| 7 | 18.4 |
| 8 | 13.1 |
| 9 | 8.0 |
| 10 | 4.6 |
| 11 | 2.7 |
| 12 | 1.7 |
| 13 | 1.1 |
| 14 | 0.8 |
| 15 | 0.5 |
| 16 | 0.5 |

EXAMPLE 6

A catalyst having compounds of the lanthanide metals and phosphorus supported on the anatase form of titanium (IV) oxide was prepared by the following procedure. To 28.2 grams of titanium oxide, which had been converted to the anatase form by calcination at 800° C. for 12 hours, were added 40.3 grams of an aqueous solution of lanthanide nitrates (1.71 mmol of lanthanides/gram of solution; 95% lanthanum, 5% a mixture of other lanthanides). The impregnated powder was calcined at 600° C. in flowing air for 5 hours. This afforded 39.0 grams of a blue solid. The solid was wetted with 100 ml of deionized water followed by the addition of 50 ml of 1.7M phosphoric acid. The slurry was allowed to react for 30 minutes. The resulting supported catalyst was isolated by filtration and washed with de-ionized water until the rinses were neutral. The powder obtained was dried in vacuo at 50° C. and 5 mm Hg to afford 42.9 grams of a white powder.

To 110 grams of NEODOL 23 Alcohol were added 4.6 grams of the supported catalyst prepared as described above. An ethoxylation reaction was then carried out according to the procedures described in Example 1. A total of 175 grams of ethylene oxide was consumed over a period of 70 minutes at 155° C. The product had a mean average adduct number of 6.2. The adduct distribution of this product is presented in the following table.

| ETHOXYLATE DISTRIBUTION | |
| --- | --- |
| Adduct Number | Concentration |
| 0 (Residual Alcohol) | 3.7% wt |
| 1 | 0.9 |
| 2 | 0.9 |
| 3 | 1.8 |
| 4 | 5.5 |
| 5 | 11.8 |
| 6 | 18.4 |
| 7 | 18.1 |
| 8 | 14.6 |
| 9 | 9.3 |
| 10 | 5.4 |
| 11 | 3.2 |
| 12 | 2.0 |
| 13 | 1.2 |
| 14 | 0.9 |
| 15 | 0.6 |
| 16 | 0.5 |

EXAMPLE 7

A catalyst having compounds of the lanthanide metals and phosphorus supported on zirconia (zirconium (IV) oxide) was prepared by the following procedure. To 30.4 grams of zirconia were added 10.5 grams of an aqueous solution of lanthanide nitrates (1.71 mmol of lanthanides/gram of solution; 95% lanthanum, 5% a mixture of other lanthanides). The impregnated powder was calcined at 600° C. in flowing air for 17 hours. This afforded 33.2 grams of a white solid. The solid was wetted with 100 ml of deionized water followed by the addition of 50 ml of 0.44M phosphoric acid. The slurry was allowed to react for 30 minutes. The resulting supported catalyst was isolated by filtration and washed with de-ionized water until the rinses were neutral. The powder obtained was dried in vacuo at 50° C. and 5 mm Hg to afford 33.5 grams of a white powder.

To 110 grams of NEODOL 23 Alcohol were added 17.3 grams of the supported catalyst prepared as described above. An ethoxylation reaction was then carried out according to the procedures described in Example 1. A total of 175 grams of ethylene oxide was consumed over a period of 65 minutes at 155° C. The product had a mean average adduct number of 5.8. The adduct distribution of this product is presented in the following table.

| ETHOXYLATE DISTRIBUTION | |
| --- | --- |
| Adduct Number | Concentration |
| 0 (Residual Alcohol) | 3.1% wt |
| 1 | 0.9 |
| 2 | 1.1 |
| 3 | 2.3 |
| 4 | 6.4 |
| 5 | 14.2 |
| 6 | 22.0 |
| 7 | 21.4 |
| 8 | 14.4 |
| 9 | 7.4 |
| 10 | 3.4 |
| 11 | 1.5 |
| 12 | 0.8 |
| 13 | 0.4 |
| 14 | 0.2 |
| 15 | 0.2 |
| 16 | 0.1 |

EXAMPLE 8

The pellets of magnesium/lanthanum oxide prepared as described in Comparative Example B below were converted into an active catalyst by treatment with phosphoric acid. Thus, 3.57 grams of the pelletized solid were wetted with 100 milliliters of distilled water. While gently stirring the supernatant solution, 50 milliliters of a 0.4M solution of phosphoric acid were added to the wetted pellets. This was allowed to react for 30 minutes at room temperature. The solid was collected by suction filtration and washed with distilled water until the rinses were neutral. The pellets were dried in vacuo at 50° C. This afforded 4.98 grams of a white solid.

To 110 grams of NEODOL 23 Alcohol were added 3.3 grams of the supported catalyst prepared as described above. An ethoxylation reaction was then carried out according to the procedures described in Example 1. A total of 175 grams of ethylene oxide was consumed over a period of 90 minutes at 155° C. The product had a mean average adduct number of 6.6. The adduct distribution of this product is presented in the following table. This Example in conjunction with Comparative Example B demonstrates the necessity for the phosphorus component in the supported catalyst.

| ETHOXYLATE DISTRIBUTION | |
| --- | --- |
| Adduct Number | Concentration |
| 0 (Residual Alcohol) | 2.9% wt |
| 1 | 0.6 |
| 2 | 0.7 |
| 3 | 1.2 |
| 4 | 3.4 |
| 5 | 8.62 |
| 6 | 16.4 |
| 7 | 20.3 |
| 8 | 17.6 |
| 9 | 11.9 |
| 10 | 6.9 |
| 11 | 3.8 |
| 12 | 2.2 |
| 13 | 1.3 |
| 14 | 0.9 |
| 15 | 0.6 |
| 16 | 0.5 |

COMPARATIVE EXAMPLE A

Twenty-five grams of the α-Alumina support material used in Example 3 were calcined at 700° C. for 5 hours. These rings were wetted in 150 ml of deionized water followed by the addition of 25 ml of 2M phosphoric acid. The supernatant of the reaction mixture was gently stirred while the supported oxide was allowed to react for 15 minutes. The resulting modified support was isolated by filtration and washed with deionized water until the rinses were neutral. The rings were dried in vacuo at 50° C. and 5 mm Hg to afford 24.9 grams of white rings.

Ten grams of these pellets were added to 110 grams of NEODOL 23 Alcohol. An ethoxylation reaction was then attempted according to the methods used in Example 1. The reaction consumed no ethylene oxide beyond what was required to initially pressurize the vessel. This demonstrates the necessity for the lanthanide component in the supported catalyst.

COMPARATIVE EXAMPLE B

To a solution of 11.0 grams of magnesium nitrate hexahydrate in 100 milliliters of water were added 25 grams of an aqueous solution of lanthanide nitrates (1.71 mmol of lanthanides/gram of solution; 95% lanthanum, 5% a mixture of other lanthanides). To this solution were added 27 milliliters of 10N ammonium hydroxide in a dropwise manner. The precipitated solid was isolated by suction filtration and washed with several portions of distilled water. The filter cake was dried at 110° C. in vacuo. The dried solid was crushed and sieved to a 20 to 50 mesh particle size. The particles were calcined at 600° C. in flowing air for 2 hours. This afforded 7.14 grams of a white solid.

These pellets (3.3 grams) were added to 110 grams of NEODOL 23 Alcohol. An ethoxylation reaction was then attempted according to the methods used in Example 1. When no apparent reaction took place after 30 minutes at 155° C. the temperature was raised to 170° C. The reaction consumed no ethylene oxide beyond what was required to initially pressurize the vessel.

What is claimed is:

1. A catalyst suitable for the preparation of alkylene oxide adducts of active hydrogen-containing organic compounds, said catalyst comprising one or more compounds of a rare earth element and phosphorus supported on an inert porous support, wherein said catalyst is prepared by impregnating an inert porous support with solution of at least one rare earth compound, calcining said support, impregnating said support with a solution of a phosphorus-containing compound, and subsequently drying to prepare catalyst.

2. The catalyst of claim 1 wherein said rare earth compound is selected from the group consisting of lanthanide nitrate, lanthanide carbonate, lanthanide chloride, lanthanide hydroxide and mixtures thereof.

3. The catalyst of claim 1 wherein said phosphorus-containing compound is phosphoric acid.

4. The catalyst of claim 1 wherein said catalyst contains from about 0.5 percent by weight to about 36 percent by weight rare earth element and from about 0.1 percent by weight to about 8 percent by weight phosphorus.

5. The catalyst of claim 1 wherein said porous inert support is selected from the group consisting of alumina, silica, silica-alumina, titania, zirconia, magnesia and mixtures thereof.

6. The catalyst of claim 4 wherein said catalyst contains from about 6 percent by weight to about 24 percent by weight rare earth element and from about 1 percent by weight to about 6 percent by weight phosphorus.

7. A process for the preparation of a catalyst suitable for the preparation of alkylene oxide adducts of active hydrogen-containing organic compounds, which process comprises impregnating an inert porous support with a solution of at least one rare earth compound, calcining said support at a temperature in the range of from about 100° C. to about 700° C., impregnating said support with a solution of a phosphorus-containing compound, and subsequently drying at a temperature in the range of from about 50° C. to about 200° C. to prepare catalyst.

* * * * *